(12) United States Patent
Johnsen

(10) Patent No.: US 7,295,649 B2
(45) Date of Patent: Nov. 13, 2007

(54) RADIATION THERAPY SYSTEM AND METHOD OF USING THE SAME

(75) Inventor: Stanley W. Johnsen, Palo Alto, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/249,619

(22) Filed: Oct. 13, 2005

(65) Prior Publication Data

US 2007/0086569 A1   Apr. 19, 2007

(51) Int. Cl.
*A61N 5/10* (2006.01)

(52) U.S. Cl. .................................................. 378/65

(58) Field of Classification Search ............... 378/65; 250/505.1; 315/505
See application file for complete search history.

(56) References Cited

U.S. PATENT DOCUMENTS

| | | | | |
|---|---|---|---|---|
| 4,627,089 | A * | 12/1986 | Menor et al. ............... | 378/157 |
| 6,459,762 | B1 * | 10/2002 | Wong et al. ................ | 378/65 |
| 7,005,809 | B2 * | 2/2006 | Whitham et al. ........... | 315/500 |
| 2003/0026384 | A1 * | 2/2003 | Hernandez-Guerra ........ | 378/65 |
| 2004/0082855 | A1 * | 4/2004 | Robar et al. ................ | 600/436 |
| 2004/0158145 | A1 * | 8/2004 | Ghelmansarai et al. ..... | 600/427 |

OTHER PUBLICATIONS

Fu et al., Delivery time comparison for intensity-modulated radiation therapy with/without flattening filter: a planning study, 49, Mar. 24, 2004, Phys. Med. Biol., 49, p. 1535-1547.*
Jingeng Zhu, Generation of wedge-shaped dose distributions through dynamic multileaf collimator dose delivery, Aug. 12, 2005, J. App. Clinical Med. Phys., vol. 6, No. 3, Summer 2005, p. 37-45.*
Rosello et al., "Virtual wedge dosimetric behavior with Monitor Units number", 2000, Proceedings of the 22nd Annual EMBS International Conference, pp. 2200-2201.*

* cited by examiner

*Primary Examiner*—Edward J. Glick
*Assistant Examiner*—John M Corbett

(57) ABSTRACT

A method of using a radiation system having a multileaf collimator ("MLC") to adjust for unevenness in the radiation emitted by the system is disclosed. By appropriately controlling the MLC in accordance with the invention the system can be operated without a flattening filter. In addition, the invention allows the system user to vary the radiation beam energy in the course of a single treatment, without the need to use or change flattening filters. A map of the uneven radiation beam intensity in the treatment area is obtained, and the map information is combined with a treatment plan to control movement of the leaves of the MLC such that each area receives the correct radiation dose.

28 Claims, 17 Drawing Sheets

US 7,295,649 B2

RADIATION THERAPY SYSTEM AND METHOD OF USING THE SAME

FIELD OF THE INVENTION

The present invention is related to radiation therapy systems and is particularly related to a radiation therapy system having a multileaf collimator and a method of using such a system.

BACKGROUND OF THE INVENTION

Radiation therapy for cancer treatment has been in use for decades. Modern radiation therapy systems typically generate high intensity x-rays by bombarding a suitable target with high energy electrons. X-rays are emitted from the target in a generally conical pattern, and are initially confined to a generally rectangular beam by moveable, x-ray blocking "jaws" in the head of the system. Typically, the patient is positioned about 1 meter from the x-ray target, and when the jaws are fully open, they define a square treatment area that is about 40 cm×40 cm at the patient plane. However, in many instances it is important to only irradiate a precisely defined area or volume conforming to a tumor, and the target site must be irradiated from multiple angles. Rarely, however, can the system jaws alone be used implement a suitable treatment plan.

Multileaf collimators ("MLCs"), such as described in the co-assigned U.S. Pat. No. 4,868,843, issued Sep. 19, 1989, to Nunan, (the disclosure of which is incorporated by reference), have been almost universally adopted to facilitate shaping of the radiation beam so that the beam conforms to the site being treated, i.e., the beam conforms to the shape of the tumor from the angle of irradiation. Subsequent to its introduction, the MLC has also been used to perform a technique known as "Intensity Modulated Radiotherapy" ("IMRT"), which allows control over the radiation doses delivered to a specific portions of the site being treated. Specifically, IMRT allows the intensity distribution of the radiation reaching the patient to have almost any arbitrary distribution. IMRT can be implemented by iteratively positioning the leaves of the MLC to provide desired field shapes which collectively deliver the desired dose distribution. This approach is static in the sense that the leaves do not move when the beam is on. Alternatively, in systems sold by the assignee of the present invention, IMRT can be implemented using a "sliding window" approach, in which the leaves of the MLC are moved continuously across the beam when the beam is on. Specifically, by adjusting the speed of leaf motion and separation of the leaves, different portions of the treatment field can be irradiated with different doses of radiation.

Heretofore, treatment planning has proceeded based on the use of a beam that is uniform within the entire treatment area defined by the jaws. However, since the x-ray beam emitted from a target is not uniform, it has been necessary to insert a "flattening filter" in the path of the emitted x-rays to achieve beam uniformity. Specifically, a flattening filter attenuates the higher intensity, central portion of the x-ray beam. A flattening filter generally comprises a solid metallic cone of x-ray absorbing material that is inserted into the path of the x-ray beam, such that the center of the cone is coaxial with the electron beam striking the target. Because a flattening filter substantially attenuates the average intensity of the x-ray beam, it can prolong the time needed to provide the desired dose.

Raw particle beams (e.g., electron beams) used in radiotherapy also vary in intensity over the relatively large area of a modern radiation therapy system and, therefore, a structure, such as a scattering foil is used to provide a flattened output beam. To date, the use of MLCs with particle beams is relatively uncommon due to scattering problems, however it is anticipated that those problems may be addressed, such that the use of MLCs with particle beams will become more common.

Many radiation therapy systems are designed to emit x-rays at different energy levels to provide different tissue penetration capabilities, thereby providing additional treatment flexibility. Thus, for example, systems sold by the assignee of the present invention are capable of delivering x-rays in the range of 4 Mev to 23 Mev. (It is noted that the x-ray energy is generally referred to in terms of the energy of the electrons which strike the target. Thus, 6 MeV x-rays refers to x-rays created by striking the target with 6 MeV electrons.) Moreover, because the intensity distribution of x-rays emitted from the target varies according to the x-ray energy, a different flattening filter must be used at each energy level. Generally speaking, higher the x-ray energy requires a thicker filter, i.e., a cone with a larger height. The need to use a different filter with each x-ray energy is an impediment to varying the x-ray energy of the beam in real time, and hence its penetration ability, during the course of treatment.

Likewise, known radiation therapy systems are capable of delivering particle beams at a plurality of energy levels, such that scattering foils, like x-ray flattening filters, must be carefully designed for a specific energy and a specific field size.

SUMMARY OF THE INVENTION

In a first aspect, the present invention is directed to a method of using a radiation therapy system comprising a multileaf collimator to provide treatment while accounting for unevenness in the beam intensity of the radiation therapy system, comprising the steps of obtaining a map of the beam intensity of the uneven output of the radiation therapy system in the proximity of the treatment area, developing a treatment plan comprising irradiating one or more selected portions of the treatment area with a calculated radiation dose, and positioning the leaves of the multileaf collimator and emitting radiation to selectively irradiate said selected portions of the treatment area, such that the calculated radiation dose is delivered to each selected area based on said map and said treatment plan. As used herein, the term radiation embraces both electromagnetic radiation such as x-rays and gamma rays, and particle beams comprising electrons, protons or heavier particles. The method is useful where the treatment plan uses intensity modulated radiotherapy, such that different areas in the treatment area receive different radiation doses. The leaves can either be positioned between emissions and maintained in a static position during emissions, or at least some of the leaves can be continuously moved while irradiating the treatment area. In accordance with a further aspect of the invention, x-rays or particle beams of different energies can be used, either to irradiate different portions of the treatment area, including continuously varying the energy of the beam.

In another aspect, the present invention is directed to a radiation therapy system having a beam generator for creating a radiotherapy beam for irradiating a treatment area distal from the beam generator, a multileaf collimator (MLC) positioned between said beam generator and said treatment area for controlling the shape and position of the beam, a control and memory system for storing one or more maps of beam intensity information concerning the unevenness in the beam generator in the proximity of the treatment area, for storing a treatment plan defining one or more selected portions of the treatment area which are to be irradiated with a calculated radiation dose, and for combining said beam intensity map with said treatment plan to create an adjusted treatment plan, an MLC control system coupled to said control and memory system, said for positioning the leaves of the multileaf collimator and a radiation beam control system coupled to said control and memory system controlling the beam generator, whereby said MLC control system and said radiation beam control system operate to implement said adjusted treatment plan.

BRIEF DESCRIPTION OF THE DRAWINGS

The foregoing aspects and the attendant advantages of this invention will become more readily apparent by reference to the following detailed description when taken in conjunction with the accompanying drawings, wherein.

Reference symbols are used in the Figures to indicate certain components, aspects or features shown therein, with reference symbols common to more than one Figure indicating like components, aspects or features shown therein. It is noted that none of the figures used to describe the present invention are drawn to scale, and various features and dimensions are greatly exaggerated to facilitate the discussion.

DETAILED DESCRIPTION

In general, the preferred embodiment of present invention is directed to method of operating a radiation therapy system having a multileaf collimator without a flattening filter or scattering foil. More generally, the invention is directed to using a multileaf collimator to adjust for substantial unevenness in the intensity of the radiation beam. As described herein, the elimination of the flattening filter facilitates application of higher radiation doses such that treatment times can be reduced. In addition, elimination of the flattening filter allows the therapist to vary the energy of the radiation beam at the same or different portions of the treatment area in real time, thereby increasing the usefulness and flexibility of the system. It will be appreciated that when using an electron or other particle beam it may be desirable to have some type of structure, such as a scattering element, to, for example, broaden the beam. However, in accordance with the present invention such a structure need not provide uniform beam intensity, and can be used at all desired beam energy levels without regard to energy dependent variations in beam intensity distribution.

Figure 1:
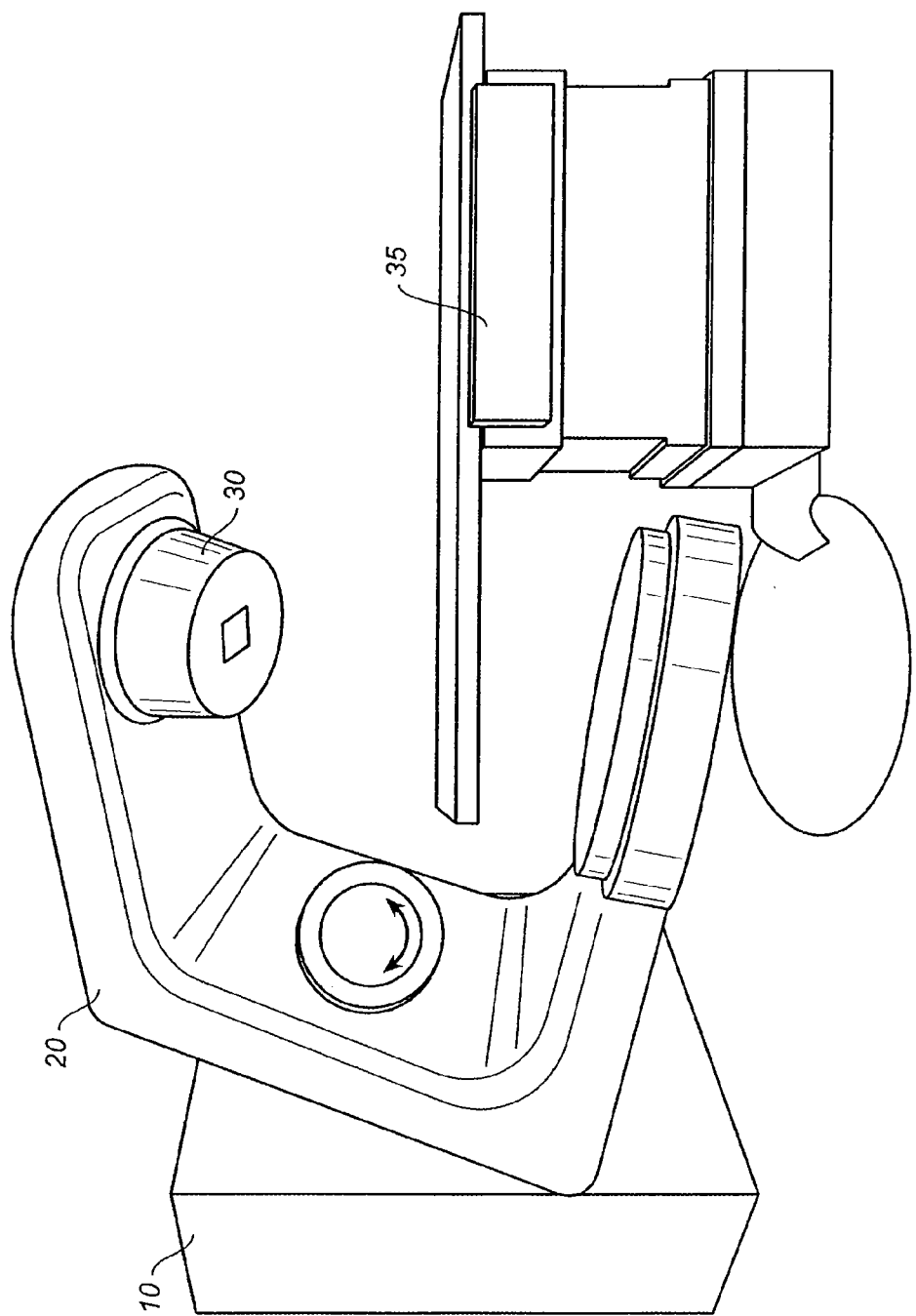
FIG. 1 is a simplified perspective view of a radiation therapy system which may be used to practice the present invention.

Referring now to FIG. 1, a radiation therapy system (sometimes referred to as a linear accelerator) which may be used to practice the method of the present invention is shown. The system may be capable of generating either a particle (e.g., electron) beam or an x-ray (photon) beam for use in the radiotherapy treatment of patients on a treatment table 35. While the present discussion will focus on x-ray irradiation, it will be appreciated that much of the discussion applies equally to particle beam radiation. Accordingly, references to a flattening filter should be understood, in context, to embrace any structure used to flatten the beam, including a scattering foil used with a particle beam.

Stand 10 supports a rotatable gantry 20 with a treatment head 30. A control unit (not shown in FIG. 1) is connected to stand 10 which includes operational electronics and computers for controlling the operation of the accelerator. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electromagnetic field within the waveguide. The electrons emitted from the electron gun are accelerated in the waveguide by the electromagnetic field, and exit the waveguide as a high energy electron beam, typically at megavoltage energies. The electron beam may be used directly to provide particle beam irradiation of the patient or the electron beam can be made to strike a suitable metal target, emitting x-rays in the forward direction, thereby providing an x-ray beam for irradiating the patient.

Figure 2:
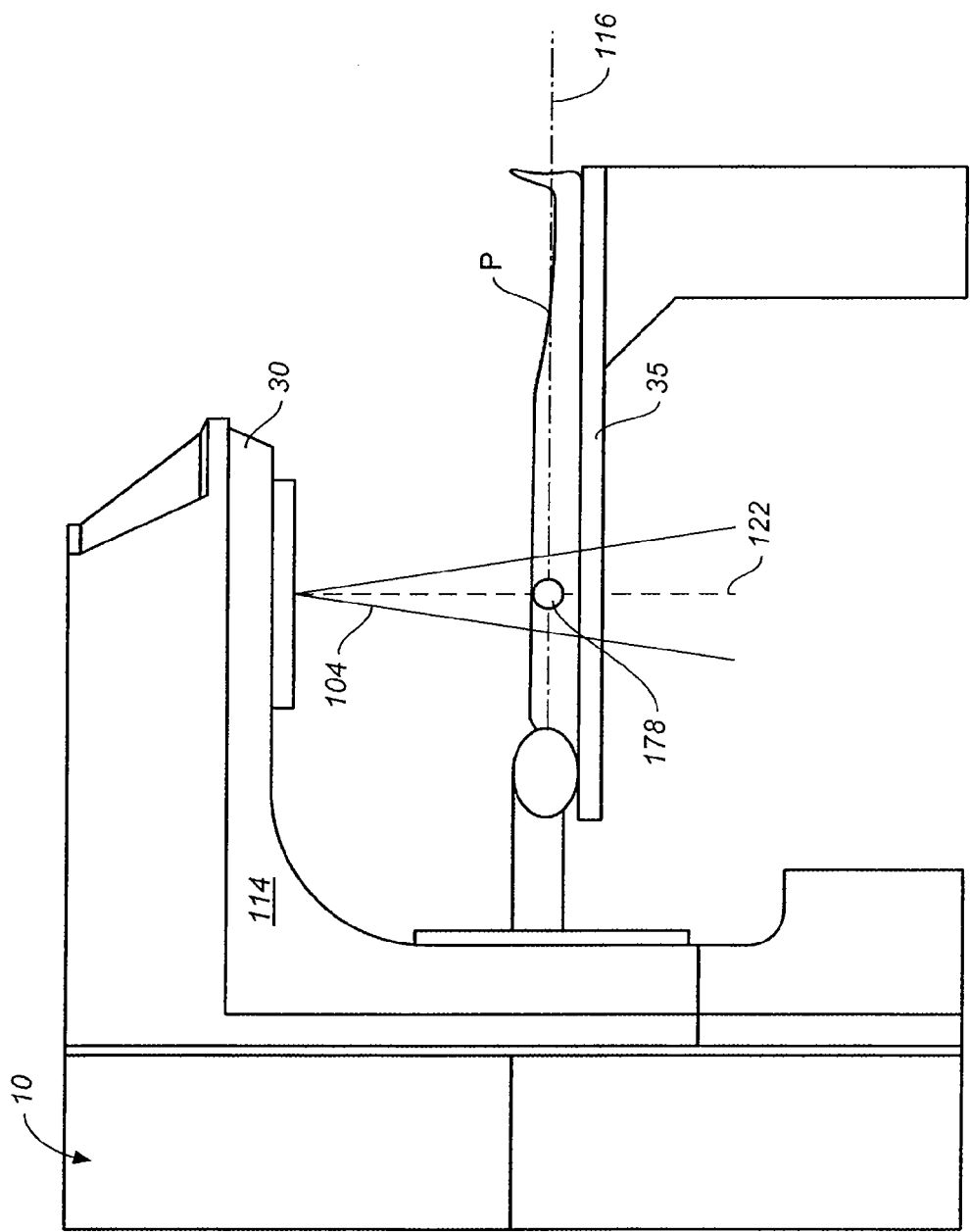
FIG. 2 is a side view of a radiation therapy system which may be used to practice the present invention.

Referring now to FIG. 2, a somewhat more detailed side view of a radiation therapy system of the type which may be used to practice the present invention is shown. A patient P is shown lying on treatment table 35. X-rays formed as described above are emitted from the target in treatment head 30 in a divergent beam 104. Typically, a patient plane 116, which is perpendicular to the page in FIG. 2, is positioned about one meter from the x-ray source or target, and the axis of gantry 20 is located on plane 116, such that the distance between the target and isocenter 178 remains constant when gantry 20 is rotated. Isocenter 178 is at the intersection between patient plane 116 and the central axis of beam 122.

As is known, "jaws" (not shown) or x-ray collimators comprising a substantial thickness of an x-ray blocking material, are positioned in head 30 to define the width of the x-ray beam at the patient plane. Typically, the jaws are moveable and, when fully open, define a maximum beam of about 40 cm×40 cm at patient plane 116. A multileaf collimator ("MLC") (not shown in FIG. 2) is positioned at the exit of head 30, to further shape the x-ray beam. Since its introduction in 1990 the MLC has become a standard feature of most radiation therapy systems. Current MLCs sold by the assignee use up to 120 individually controllable leaves, typically thin slices of tungsten, that can be moved into or out of the x-ray beam under the control of system software. A characteristic of an MLC is that it comprises a plurality of opposing leaf pairs, with each leaf in the pair capable of independent movement, such that the size and position of the opening (if any) between opposing leaves can be controlled. As described above, the MLC can be used in a known manner to collimate the x-rays to provide conformal treatment of tumors from various angles, as well as intensity modulated radiotherapy ("IMRT"), whereby different radiation doses are delivered to different portions of the treatment area. The treatment area, i.e., the irradiated area proximate to the isocenter and perpendicular to the x-ray beam, is defined by the jaws and the MLC. In IMRT, and in the present invention, the leaves of the MLC are moved, such that the treatment area comprises the total area exposed during the course of a treatment. In connection with the present invention, it is contemplated that the maximum potential treatment area will have a substantial two-dimensional extent, i.e., it extends at least several tens of centimeters in the x and y directions (relative to the beam which, for present purposes, defines the z-direction), such that variations in the unflattened beam intensity over the maximum treatment area would be significant.

Figure 3A:
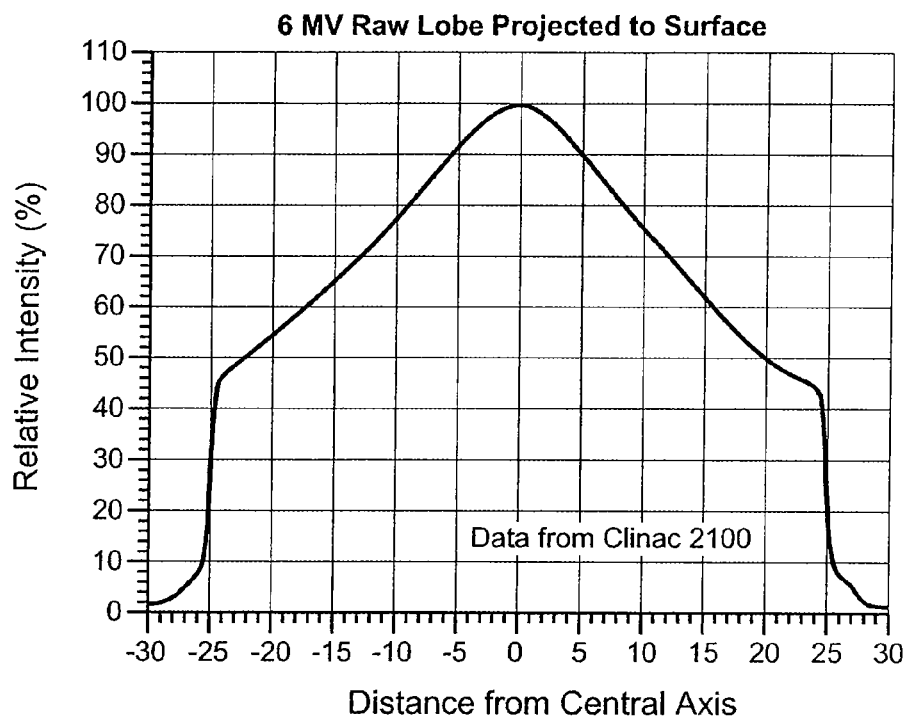
FIG. 3A is a graph of the unflattened intensity distribution of 6 MeV x-rays at the patient plane from an exemplary radiation therapy system.
Figure 3B:
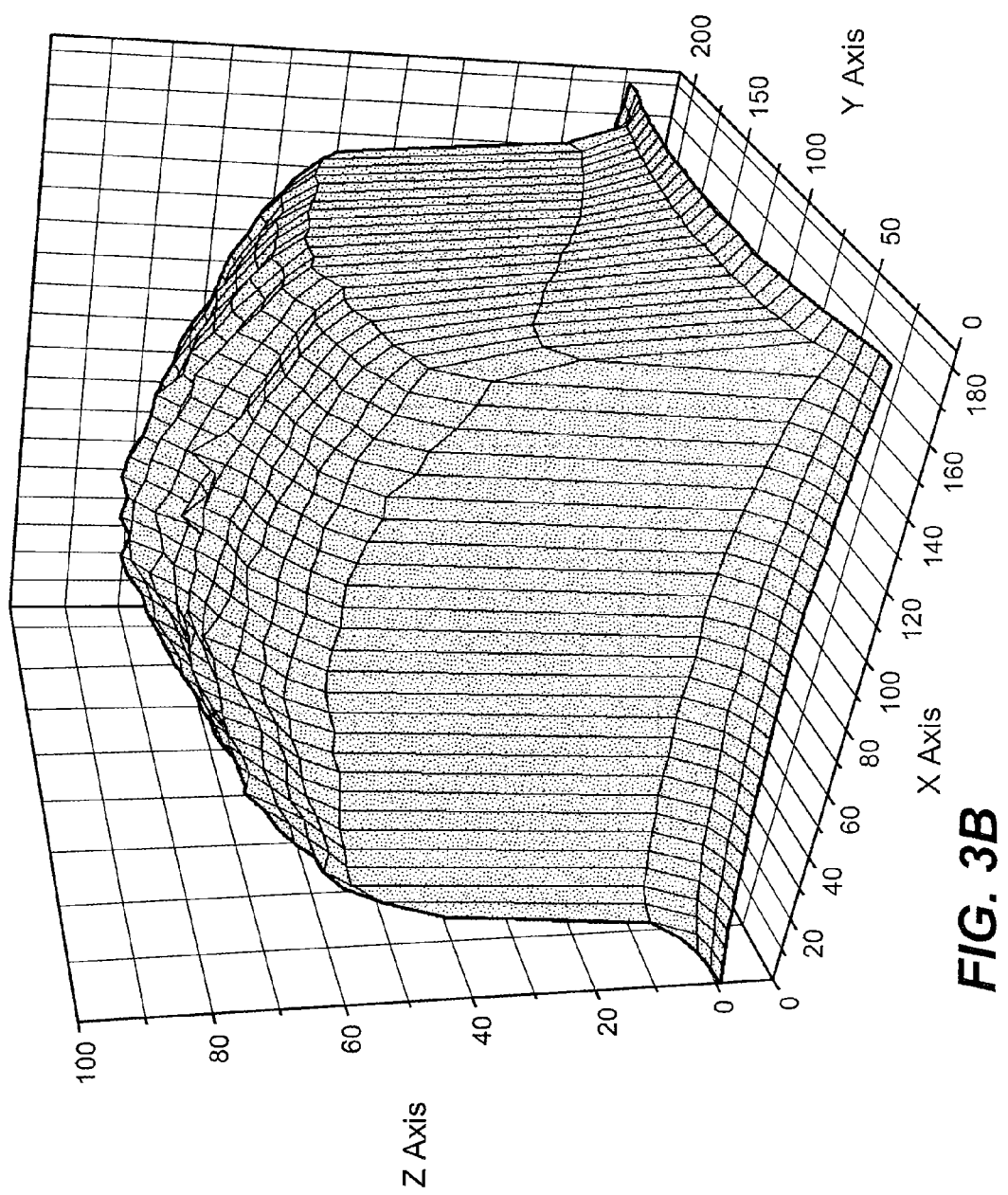
FIG. 3B is a three-dimensional image of the measured x-ray intensity at the patient plane from an unflattened beam.
Figure 3C:
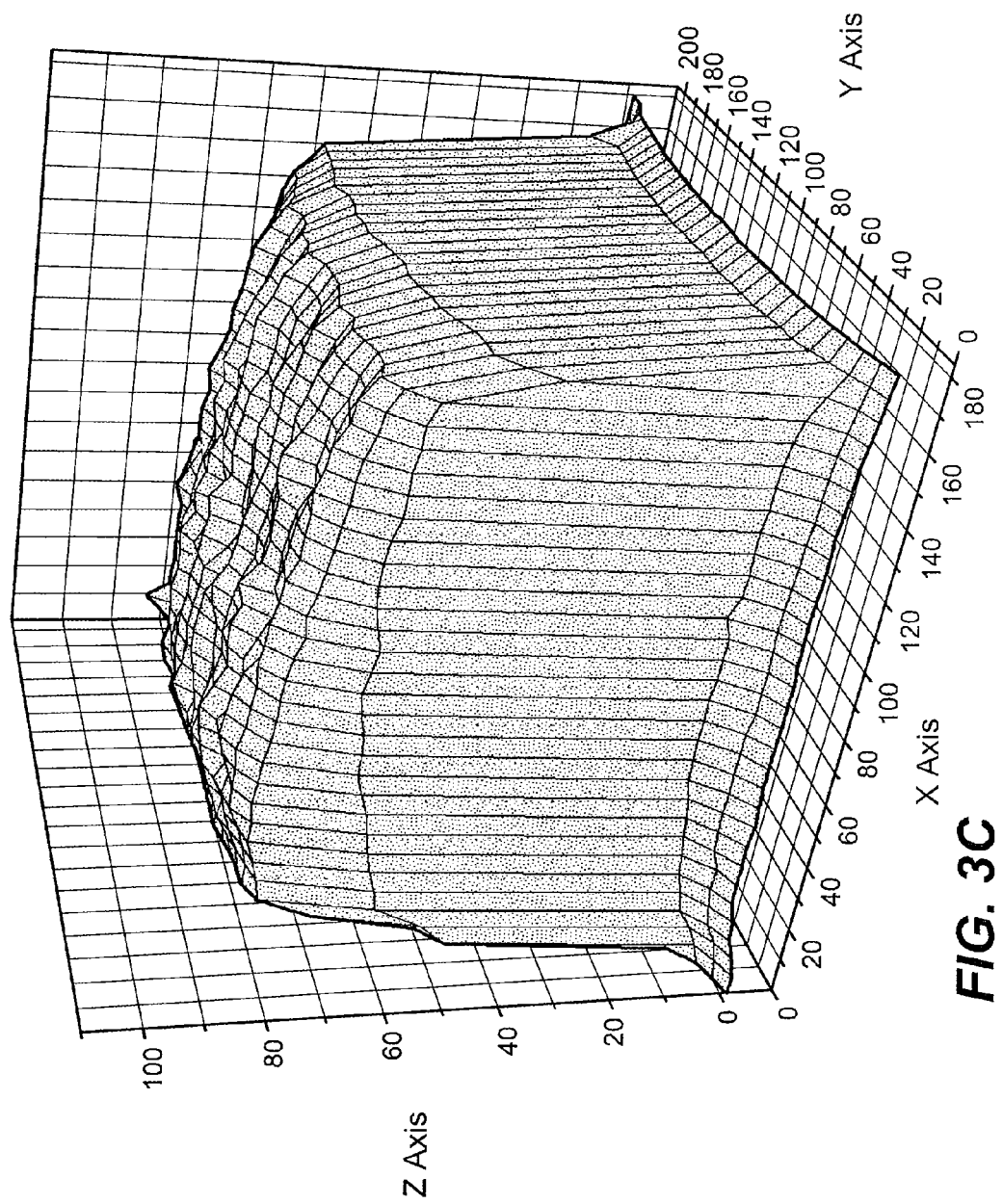
FIG. 3C is a three-dimensional image of the measured x-ray intensity at the patient plane from a beam using a flattening filter.

Radiation therapy normally requires treatment beams of substantially uniform intensity, and radiation planning techniques and software assume beam uniformity. Heretofore, known radiation therapy systems capable of irradiating a substantial two-dimensional treatment area have always used a flattening filter in the path of the radiation beam, typically between the x-ray target and the jaws, in order to provide a uniform radiation beam in the treatment area. A flattening filter has been necessary because x-rays emitted from the target are not uniformly distributed, as depicted in FIGS. 3A and 3B. FIG. 3A depicts the x-ray intensity of 6 MeV x-rays at the patient plane for a treatment area that extends roughly ±25 cm from central axis 122 of the x-ray beam. As depicted in FIG. 3A, the x-ray intensity at the center is nominally 100%, but falls off to approximately 45% of this maximum value at the edges of the field, 25 cm from the central axis. This distribution is sometimes referred to as the raw lobe of x-rays. The intensity distribution is a function of the x-ray energy, such that for 20 MeV x-rays, the intensity at the edge is only about 10% of the intensity at the central axis. FIG. 3B shows a three dimensional image of the x-ray intensity in the treatment area of an unflattened x-ray beam, as measured by the inventor. In contrast, FIG. 3C shows a three dimensional image of the x-ray intensity in the treatment area of an x-ray beam flattened using a flattening filter, as measured by the inventor. The intensity surfaces depicted in FIGS. 3B and 3C are locally irregular due to noise associated with film density measurements. As noted, raw particle beams exhibit similar non-uniform intensity distributions.

Essentially, a flattening filter comprises substantially conical mass of x-ray blocking material that is used to attenuate the high intensity central portion of the raw lobe. A cross section of the conical shape of a 6 MeV flattening filter closely matches the intensity distribution shown in FIG. 3A so as to complement the distribution. The use of higher energy x-rays requires a flattening filter defining a steeper cone—i.e., a cone with greater height. It will be appreciated that a substantial portion of the x-ray intensity is lost to the flattening filter, thereby limiting the available dose rate that can be delivered by the system. In addition, the fact that different flattening filters are required for different x-ray energies has made it impractical to vary the x-ray energy in a single treatment. Accordingly, existing radiation therapy systems that are capable of providing a plurality of different x-ray energies have a corresponding plurality of flattening filters. These are normally positioned on a carousel in head 35, and rotated into position in the path of the x-ray beam as needed. As described above, the energy of the x-rays determines how deeply the x-rays will penetrate into the tissue before being absorbed. However, because many tumors vary in depth, it would be desirable to be able to adjust the x-ray energy, and hence penetration, in the course of a single treatment.

Modern radiation therapy techniques involve the use of a treatment plan to irradiate a desired volume, usually corresponding to a tumor, with a desired dose of radiation. Most treatment planning involves the use of the MLC to provide conformal and/or intensity modulated irradiation. Generally speaking, a treatment plan comprises irradiating one or more selected portions of the treatment area with a calculated dose of x-rays, and often involves irradiating a treatment area from a plurality of different angles. Various treatment planning software and other tools are available to the therapist to develop specific treatment plans, and the details of the various techniques for creating such plans are known and need not be described in further detail. Again, generally speaking, once a treatment plan is created it is implemented, in part, by controlling the leaves of the MLC so as allow the desired radiation dose to reach the selected portions from the selected angles. Since the beam diverges from a single source, the MLC is designed to project a radiation beam with a cross-sectional area forming an irregular two dimensional shape. This maximizes use of the total radiation generated by the source to irradiate the desired shape in the treatment area, resulting in the shortest possible treatment duration with the least shielding. In the simplest treatment plan, the MLC is adjusted to provide static conformal irradiation of a specific site using a two-dimensional irregular beam shape from a single angle. In more complex plans, as briefly noted above, the site can be irradiated from a variety of different angles, with beam shaping varying from angle to angle. In IMRT the leaves can be adjusted iteratively into different positions while the beam is off, and then irradiating the site, such that the leaves form a static irregular two-dimensional shaped beam during x-ray emission, or they can be continually moved during irradiation, forming a beam that is continually changing in shape. Heretofore, treatment planning and the corresponding MLC control have proceeded on the basis that the x-ray beam is uniform, i.e., on the basis that the system has a flattening filter tailored to the x-ray energy of the beam.

The method of the preferred embodiment of the present invention uses control of the MLC to account for unevenness in radiation intensity, thereby eliminating the need to use a flattening filter. The method of the present invention allows higher x-ray doses to be delivered to the site undergoing treatment because it eliminates or reduces the substantial beam attenuation caused by the flattening filter. The method further allows the x-ray energy to be varied in real time in the course of a single treatment because it eliminates the need to change the flattening filter when changing the x-ray energy. The x-ray energy can be varied at one or more specific portions of the treatment area, such that the same portions(s) receive x-rays of different energies, or the energy can be varied at different portions of the treatment area, such that the different portions are irradiated by x-rays of different energy.

FIGS. 4A-4K show the sequential positioning of the leaves of an MLC as they are moved laterally across the x-ray beam in accordance with one embodiment of the method of the present invention. Movement of the leaves in this manner emulates a "sliding window" that moves across the x-ray beam. By appropriately separating a plurality of opposing leaves a "window" is created by the MLC, and the shape and position of this window changes as the leaves travel across the beam.

FIGS. 4A-4K show a sequence of "snapshots" at eleven periodic intervals as the leaves of the MLC are moved in continuous fashion laterally across the beam from left to right. For illustrative purposes, the sequence depicted shows leaf positions associated with providing uniform irradiation of a generally square treatment area by an unflattened x-ray beam. In other words, in the positioning of the leaves are adjusted in accordance with an embodiment of the present invention as they are moved to directly account for variations or unevenness in the beam intensity, to provide a uniform radiation dose to the entire treatment area without a flattening filter. It will be appreciated that the opening or "window" in the leaves defines the portion of the treatment area that is irradiated at a specific point in time.

Figure 4A:
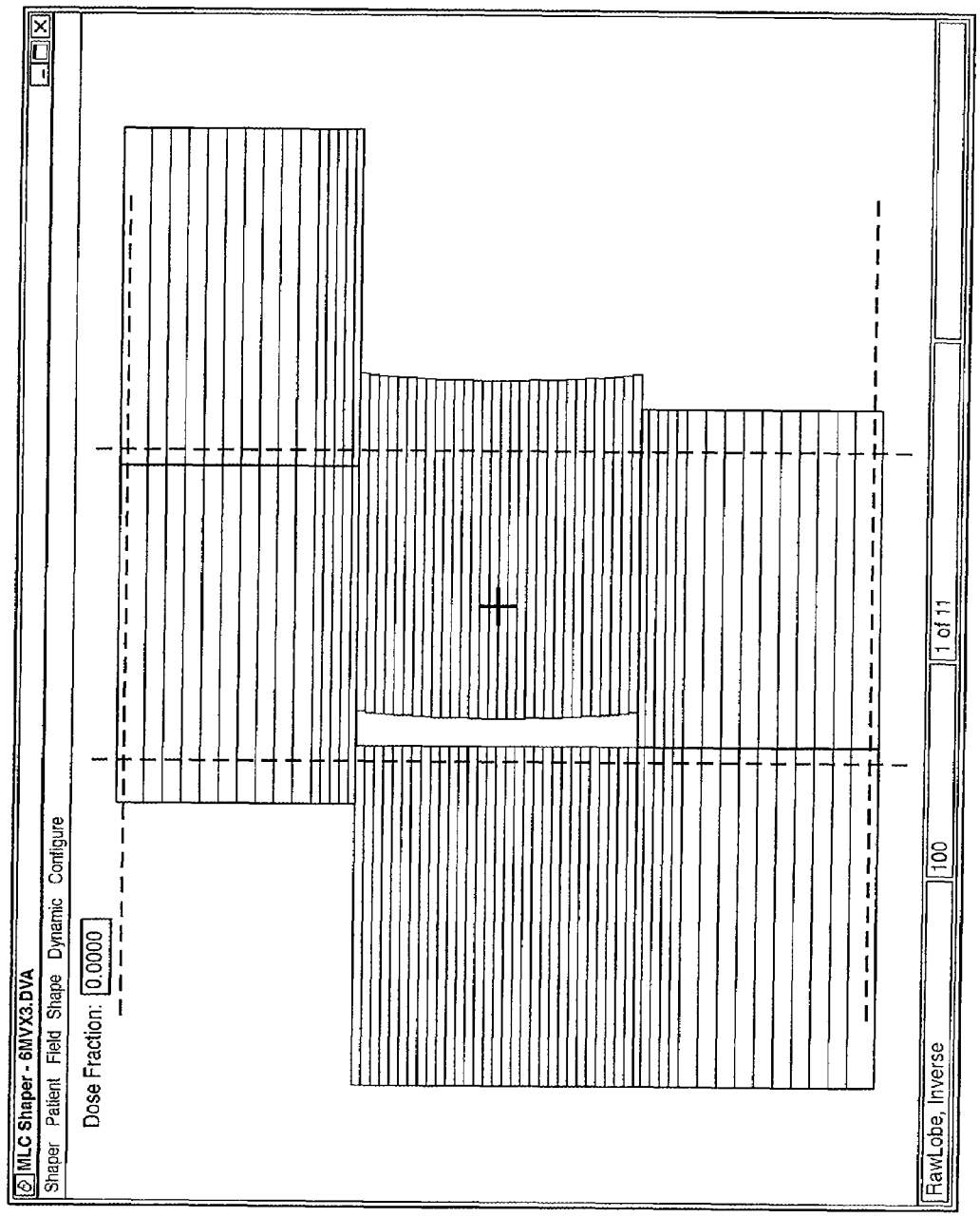
FIGS. 4A-4K depict the positioning of the leaves of a multileaf collimator in a sequence of locations calculated to deliver a uniform dose of radiation across a treatment area in a radiation therapy system without a flattening filter.
Figure 4B:
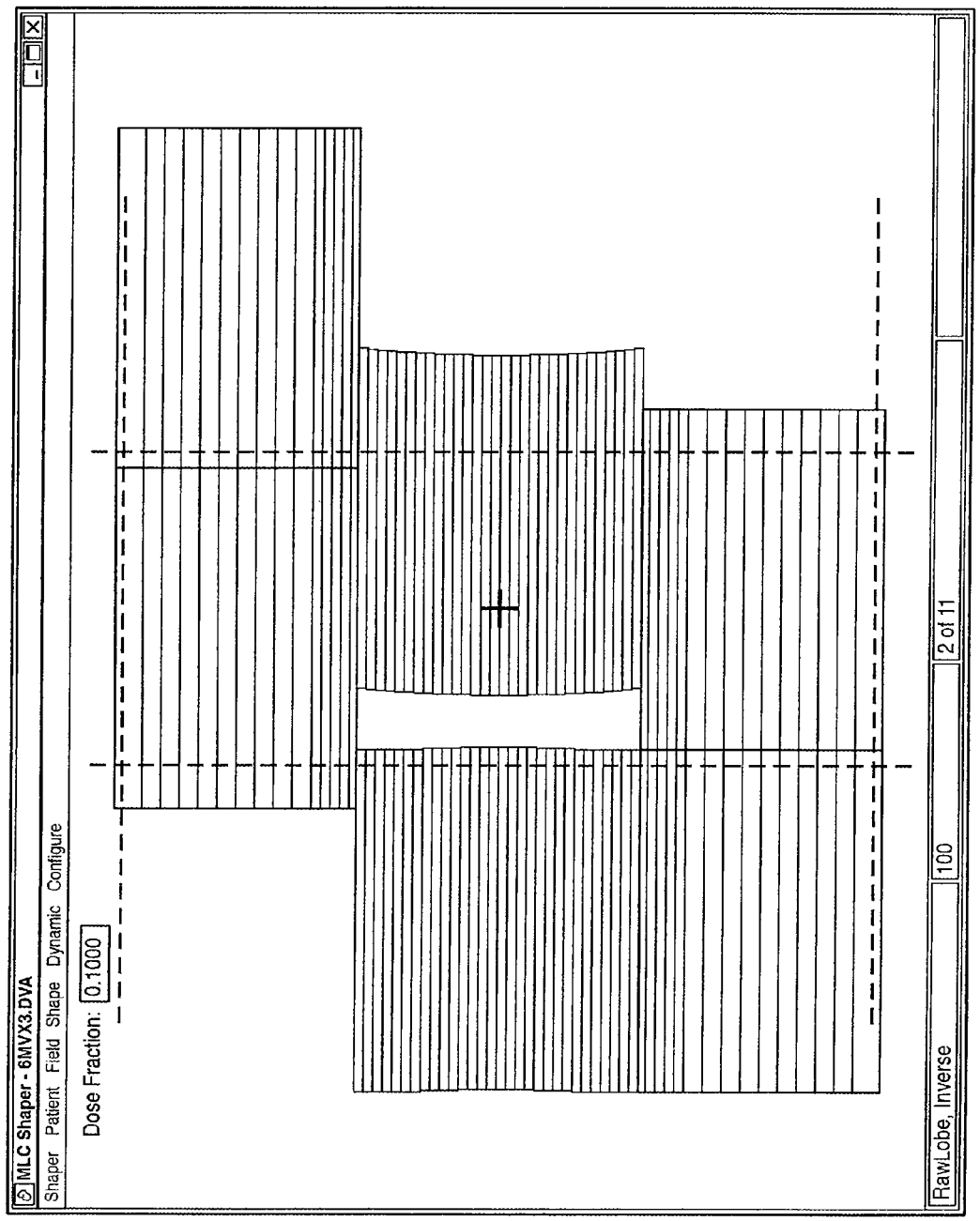
Figure 4C:
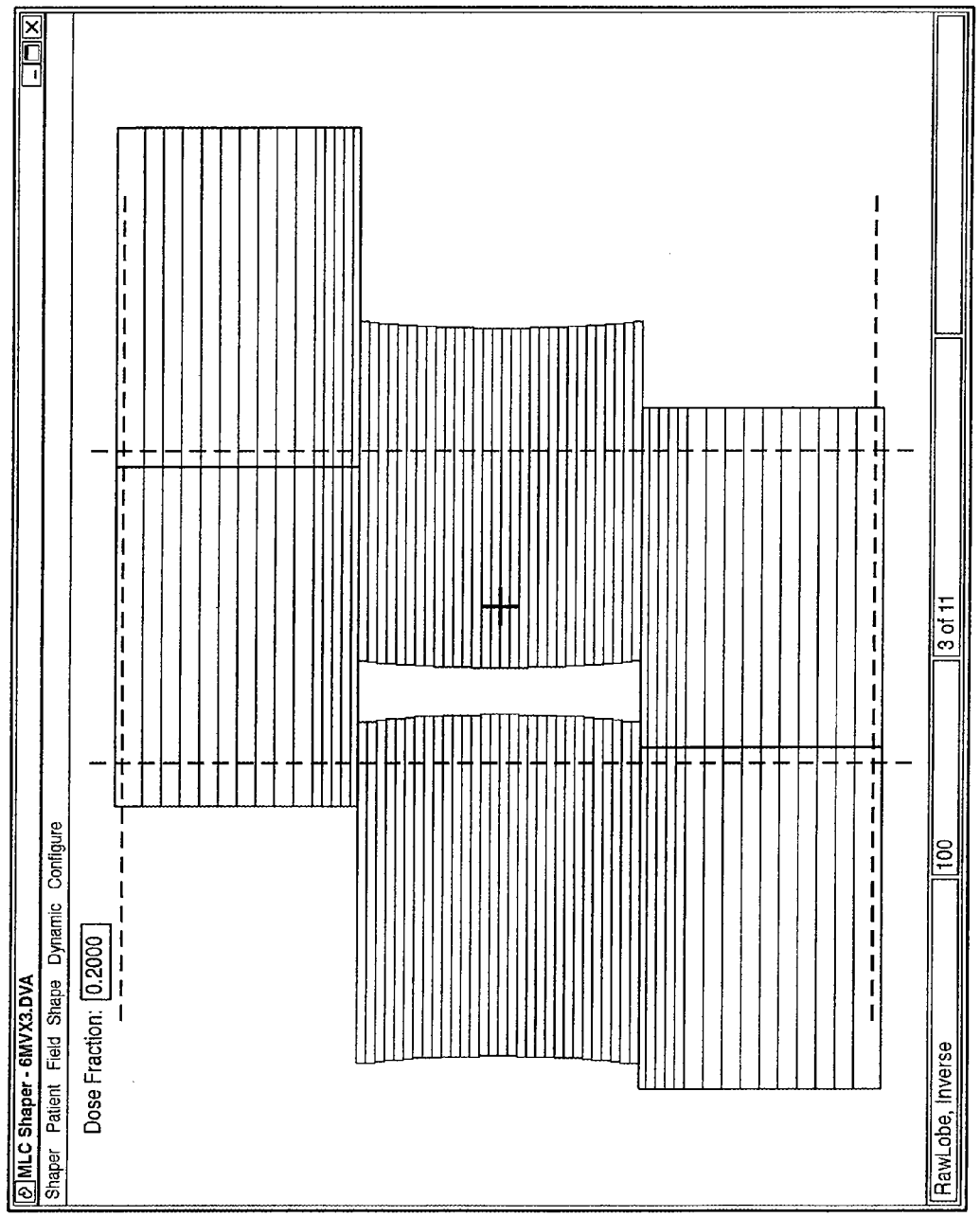
Figure 4D:
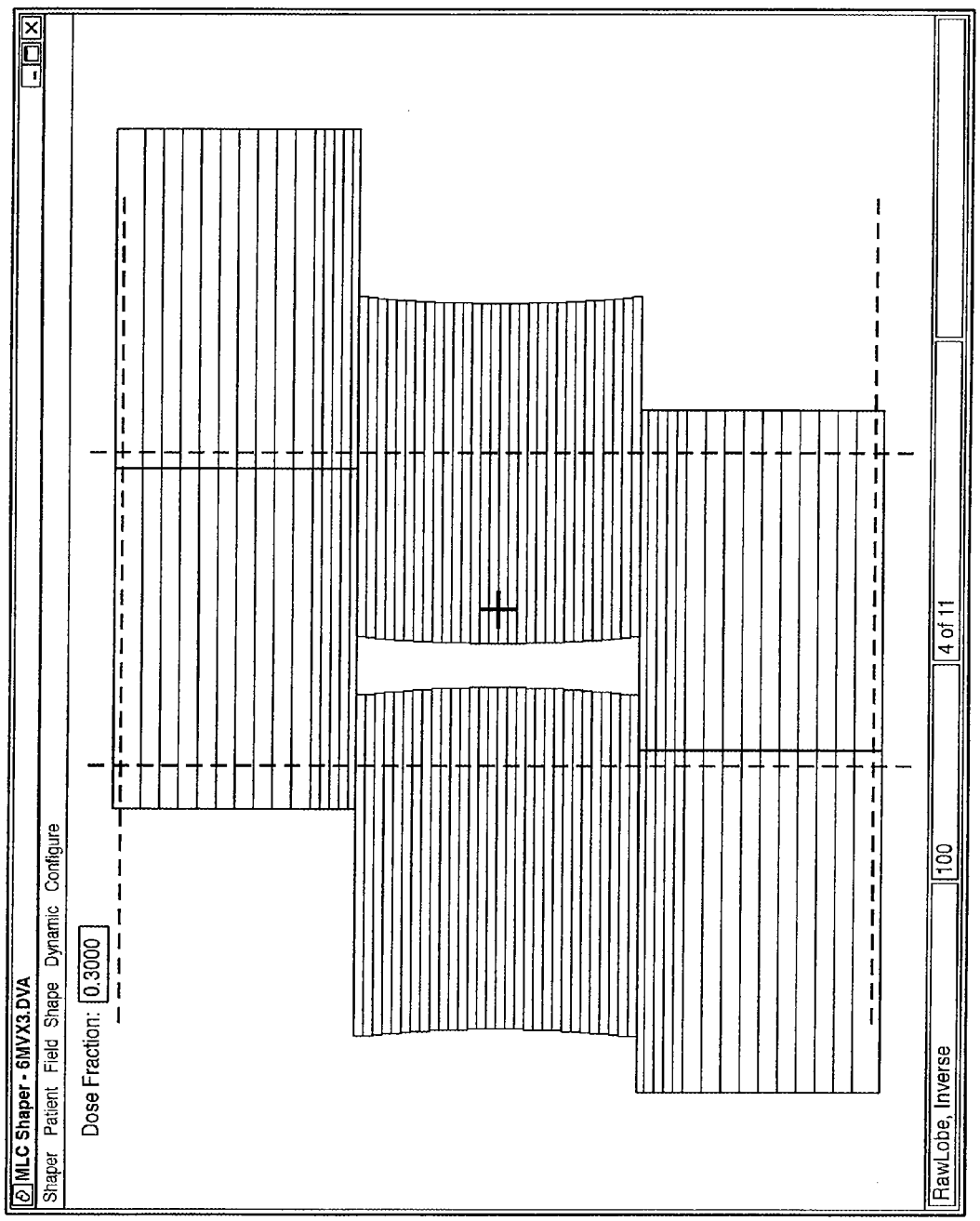
Figure 4E:
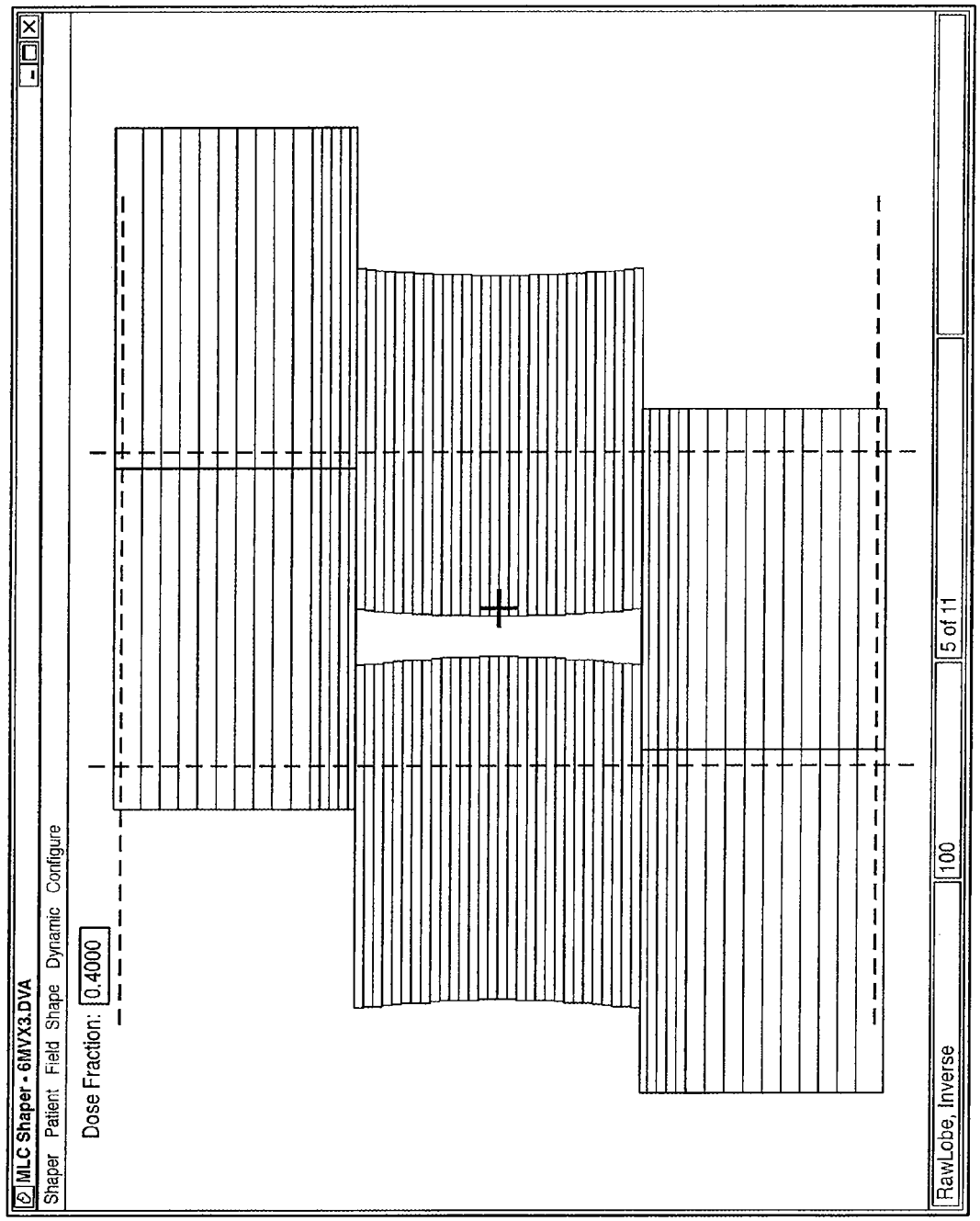
Figure 4F:
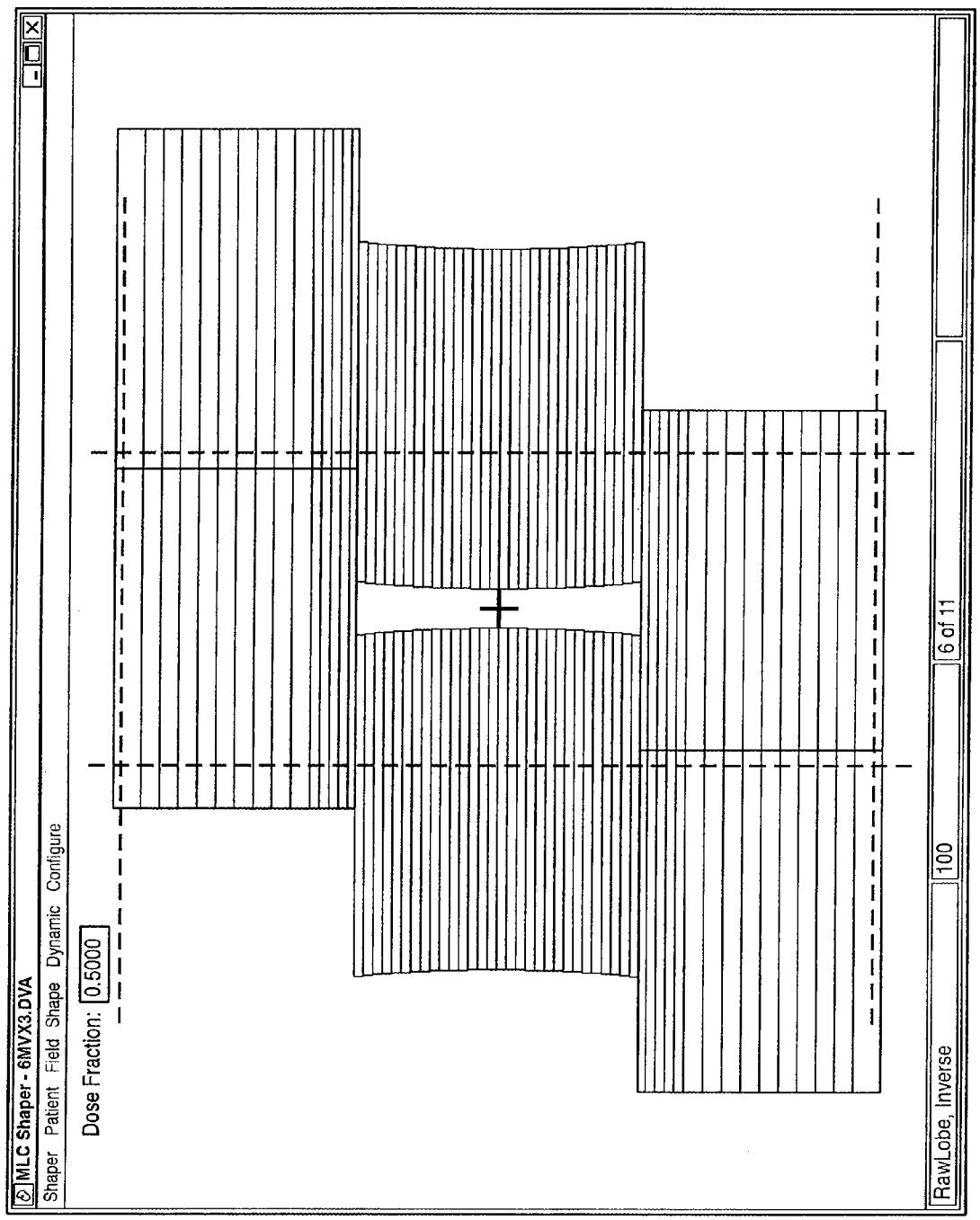
Figure 4G:
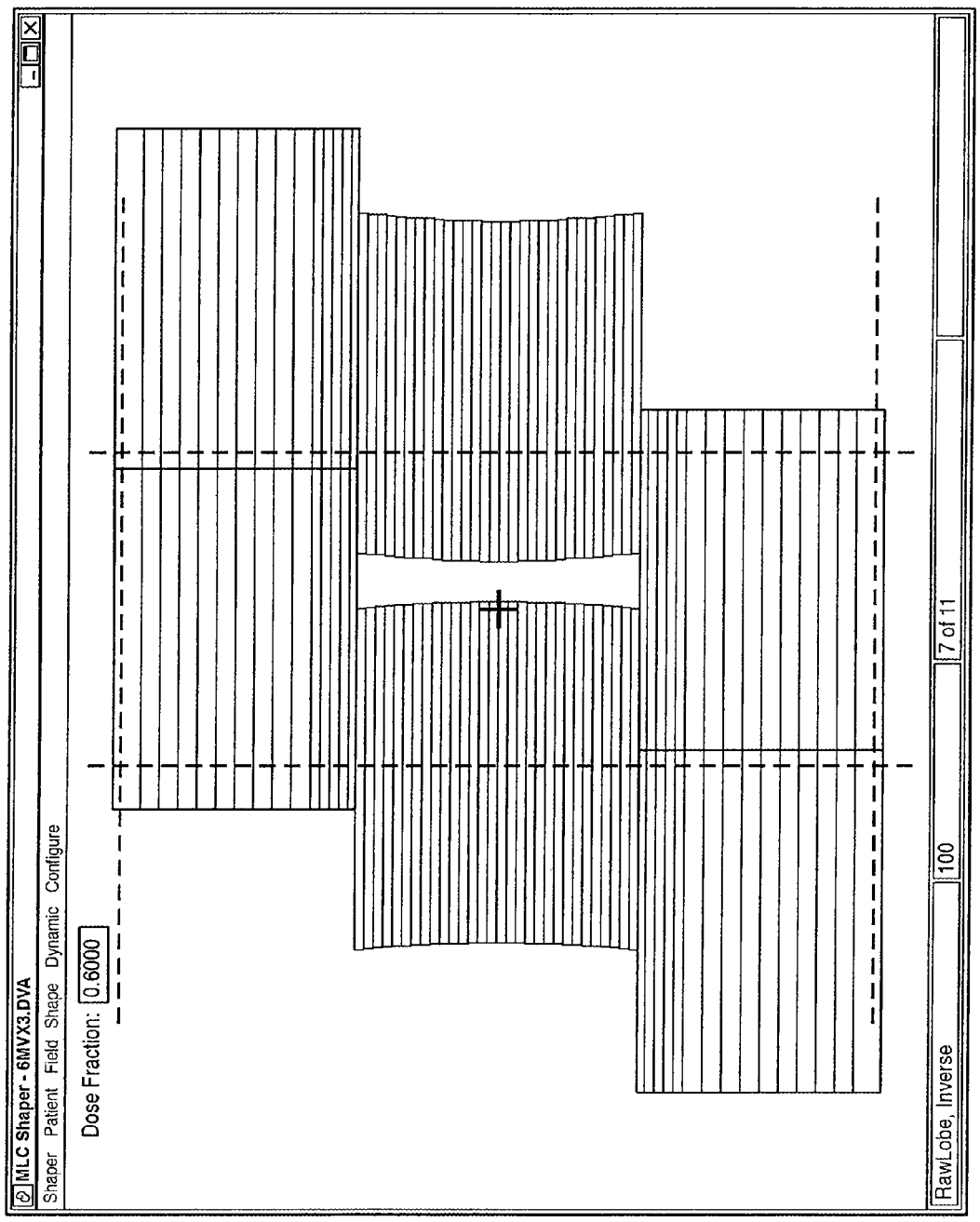
Figure 4H:
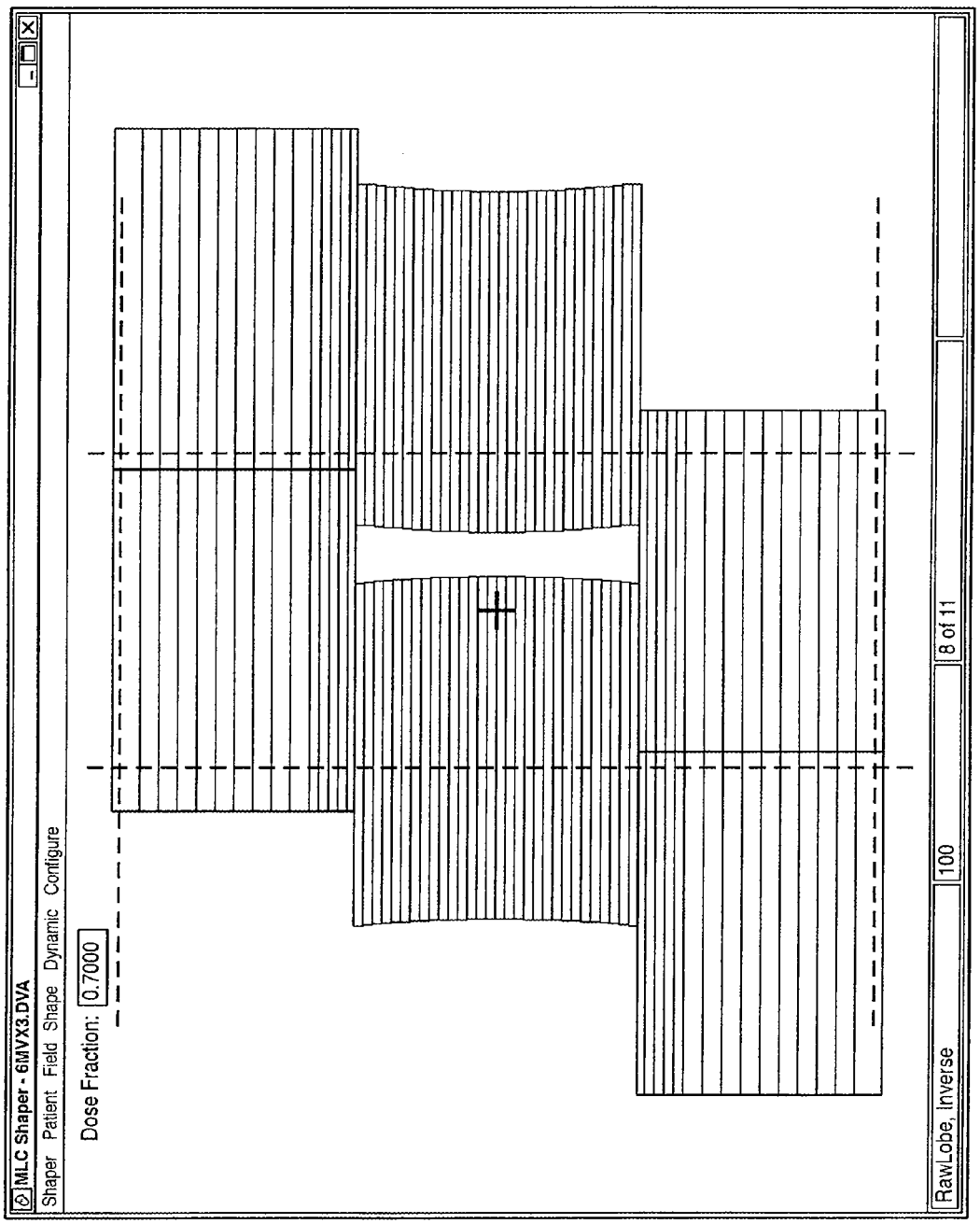
Figure 4I:
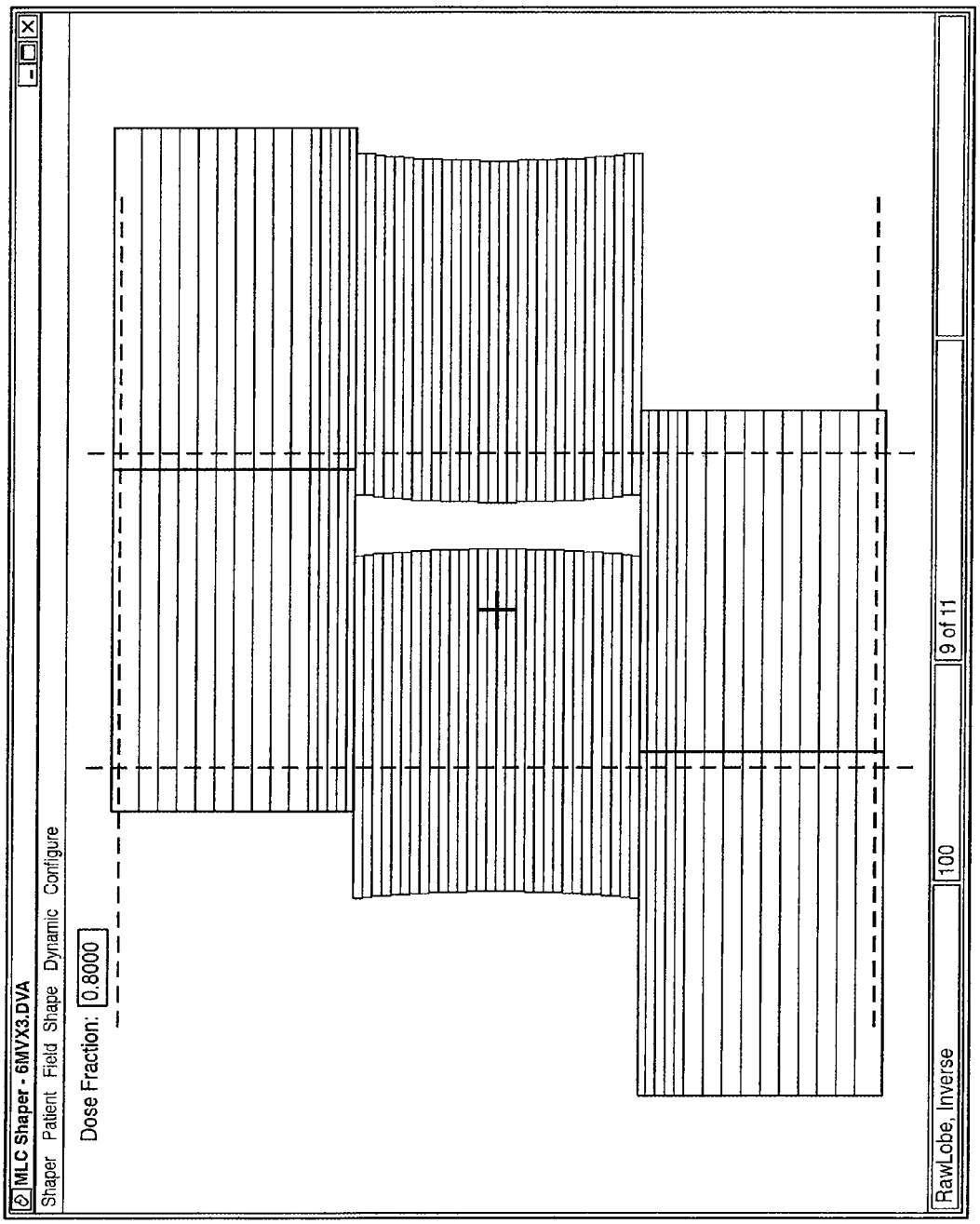
Figure 4J:
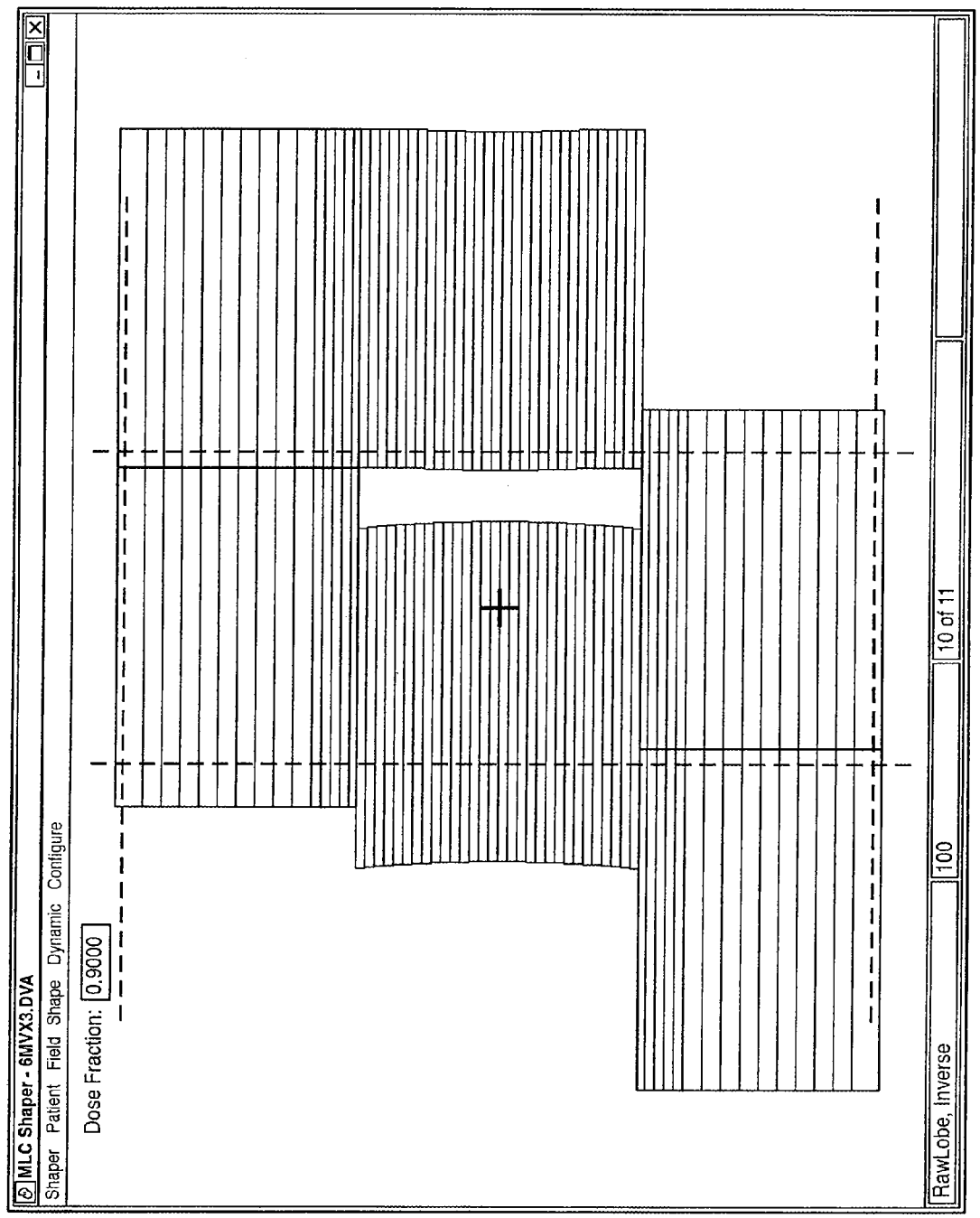
Figure 4K:
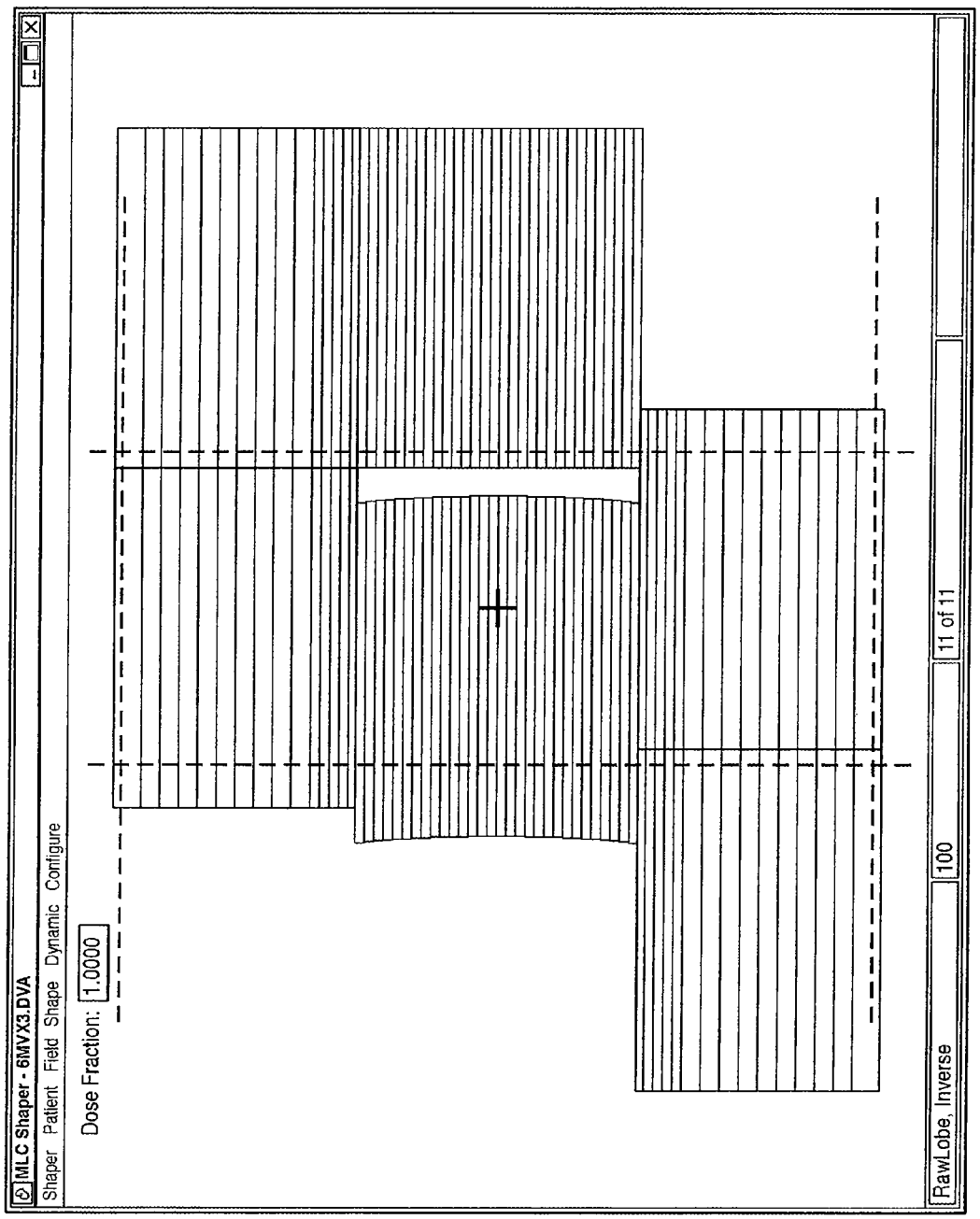

FIG. 4A shows the MLC leaves in their initial position. There is a slight curvature in the left portion of the leaf array because the beam has lower intensity in areas distal from the center of the treatment area and, as a consequence, the beam has to be "on" for a longer period of time in these regions in comparison to the center of the field. FIGS. 4B-4K show leaf positioning at subsequent times, with FIG. 4F showing the position at the halfway point, and FIG. 4K showing the final position. Because the x-ray beam intensity distribution is substantially circularly symmetrical and the leaves are moved to provide a uniform dose, the leaf positions of FIGS. 4G-4K are the mirror image of the positions of FIGS. 4A-4E. Overall, it can be seen that the leaves are arranged to create a window with a characteristic "bowtie" shape, which is most pronounced when the leaves are at the center of their travel, as shown in FIG. 4F.

Figure 5:
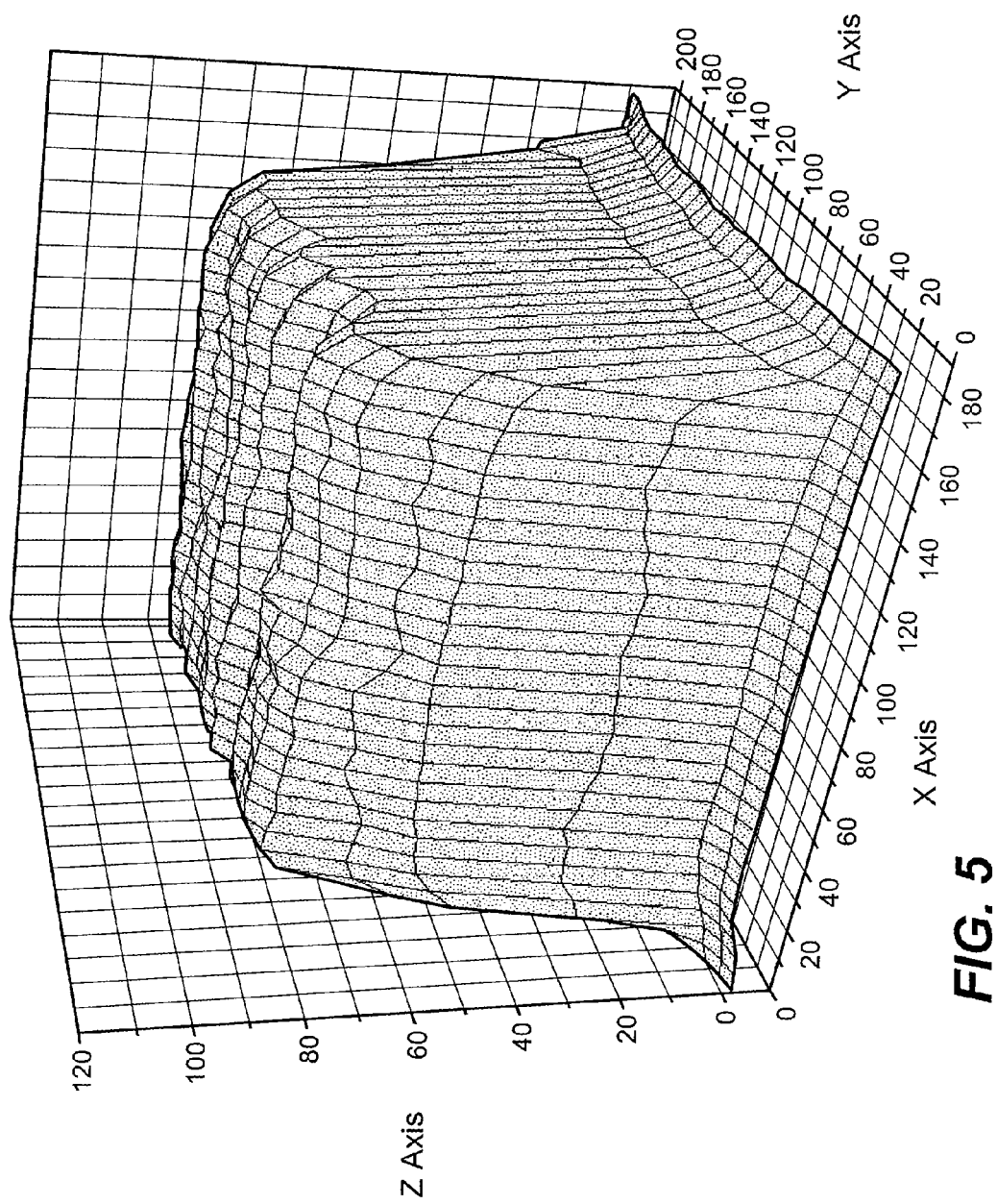
FIG. 5 is a three dimensional image of the measured x-ray intensity at the patient plane of an x-ray beam flattened using an MLC.

According to an embodiment of the present invention, if the radiation intensity at the edge of treatment field is, for example, 80% of the intensity at the center, then the sliding window is left "open" at the edge for 125% (i.e., 1/0.8) of the time it is left open at the center. It will be appreciated that the intensity distribution associated with the raw lobe of a particular x-ray beam will vary depending on a number of factors, including, for example, the energy of the x-rays. Therefore, prior to programming the movements of the leaves, for each x-ray energy level, it is necessary to obtain a map of the x-ray intensity distribution of the raw lobe in the treatment area. Such a map can be generated by the system user or can be supplied to the user by the system manufacturer using well-known techniques. Preferably intensity mapping will be performed periodically in order to ensure that the information remains accurate over time. FIG. 5 shows a three dimensional image of the x-ray intensity in the treatment area of an x-ray beam without a flattening filter, but flattened using only an MLC, as measured by the inventor. Again, the surface irregularities are noise due density measurements.

While the above discussion of FIGS. 4A-4K was, for illustrative purposes, directed to uniformly irradiating a square treatment area at a single x-ray energy, the technique can be generalized to provide IMRT and/or conformal treatment of an area of almost any desired shape from any angle without a flattening filter. Additionally, the treatment area does not need to be uniformly irradiated, but as will be described in more detail below, can have any desired fluence distribution by virtue of MLC leaf positioning. Moreover, the technique can be generalized to irradiate the same or different areas with x-rays of different intensities. In its generalized form, the present invention involves the combination of a treatment plan which defines the areas to be irradiated, the radiation dose for each area, and the x-ray intensity(ies) at each area, with map information about the raw lobe of the x-ray beam for each intensity in the treatment plan. Movement of the MLC leaves is then calculated based on this combination.

Methods of controlling the leaves of an MLC to provide a desired radiation dose to selected portions are known and need not be described in detail. In one embodiment, the MLC control software divides the desired radiation dose into fractions and the leaves are programmed to be at specific points for each fraction of the total irradiation period. Thus, at each fraction the leaves are at specific "waypoints" along their path. Each waypoint defines what is generally referred to as a field "segment." The total exposure to be delivered is programmed into the machine, setting the dose for each segment. Thus, exemplary FIGS. 4A-4K show eleven segments, and the leaf drive speed is adjusted so that when each waypoint is reached the leaves are at the desired position and the proper dose of radiation has been delivered. In essence, the treatment area can be viewed as defining an array of pixels, and as the window moves across the beam various pixels are irradiated. Movement and shaping of the window are controlled by moving the individual leaves, such that each pixel receives the desired radiation dose. In determining the how long a pixel in the treatment area should be irradiated, the present invention uses and combines information from the intensity map and from the treatment plan.

In a further embodiment of the invention, the energy of the x-rays is continuously varied during a single treatment. Continuous variation of the x-ray energy can achieved by continuously varying the energy of the electron beam. When implementing the method of this embodiment it is not necessary to obtain a map of the unfiltered energy at every possible energy level. Rather, a plurality of intensity distribution maps corresponding to a plurality of energy levels are obtained, and this plurality of maps is interpolated, as necessary, to generate a map at any intermediate energy level. Of course, a larger the number of maps will yield more accurate interpolations.

Figure 6:
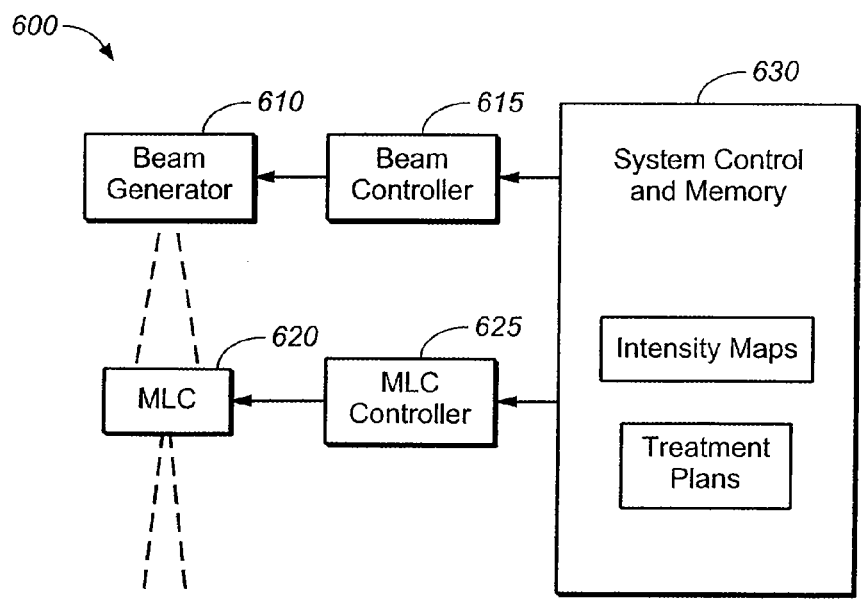
FIG. 6 is a schematic diagram of a radiotherapy system according to the present invention, to show certain control features.

FIG. 6 is a schematic diagram of a radiotherapy system 600 according to an embodiment of the present invention, to show the control features. System 600 comprises a beam generator 610 for creating a radiotherapy beam under the control of a radiation beam control system 615, and a multileaf collimator 620 for controlling the shape and position of the beam under the control of a MLC control system 625. Both the beam generator and the MLC have previously been described. System 600 comprises a control and memory system 630, such as a system computer, in which any beam intensity maps are stored. In addition, control and memory system 630 stores the treatment plan parameters, and combines the intensity map information with the treatment plan information to create an adjusted treatment plan, in other words a treatment plan which takes into account the map information and the treatment plan parameters. Control and memory system 630 then sends appropriate control information to beam control system 615 and MLC control system 625 to implement the adjusted treatment plan. It will be appreciated that the control system can be implemented in various ways. Thus, while various control systems are described as distinct systems, one or more of them can be combined in a single computer system.

While the preferred embodiment has been described in connection with a system that has no flattening filter, the present invention can also be used advantageously in connection with a system that has a flattening filter. For example, in another embodiment the system has a single flattening filter, such as the one that is used to provide beam uniformity at the most commonly utilized x-ray energy. In such a system, the method of the present invention can be used to adjust the beam to provide the desired dose at higher or lower energies by using the MLC, without the need to interpose a different flattening filter in the beam path. In addition, even if a filter is present, the technique of the present invention can be used, as described above, to enable varying the x-ray energy in the course of a single treatment. The present invention also contemplates the use of other filters. For example, a filter might be used to provide some beam shaping, or to block the electron beam from reaching the patient in case the x-ray target is moved out of position.

As noted, it is contemplated that the present invention will also be applicable to particle beam therapy, which has the same issue of non-uniformity of the beam. While the use of MLCs with particle beams is still relatively uncommon, it is anticipated that this may change, such that the benefits of the present invention will have direct application. Likewise, the invention has application to photonic beams other than x-rays generated by electron bombardment of a target, for example, gamma radiation from a radioisotope. Moreover, radiation therapy is used in its broadest sense, and includes radiosurgery.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A method of using a radiation therapy system comprising a multileaf collimator to provide treatment while accounting for unevenness in the intensity distribution of the beam of the radiation therapy system, comprising,
    obtaining a map of the unevenness in the intensity distribution of the beam of the radiation therapy system in the proximity of a treatment area at at least one beam energy level,
    developing a treatment plan comprising irradiating one or more selected portions of the treatment area with a calculated radiation dose,
    positioning the leaves of the multileaf collimator and emitting radiation to selectively irradiate said selected portions of the treatment area, such that the calculated radiation dose is delivered to each selected portion based on said map and said treatment plan
    wherein said treatment plan comprises irradiating different portions of the treatment area with different beam energy levels, and wherein the step of irradiating different portions of the treatment area with different beam energies comprises continuously varying the energy of the beam.

2. The method of claim 1 wherein said treatment plan comprises intensity modulated radiotherapy, such that different portions of the treatment area receive different radiation doses.

3. The method of claim 1 wherein said step of positioning the leaves of said multileaf collimator comprises iteratively positioning the leaves in between radiation emissions and maintaining them in a static position during emissions.

4. The method of claim 1 wherein said step of positioning the leaves of said multileaf collimator comprises continuously sliding at least some of the leaves while emitting radiation.

5. The method of claim 1 wherein the beam is an x-ray beam.

6. The method of claim 1 wherein said treatment plan further comprises irradiating the same portion of the treatment area with a beam at different energy levels.

7. The method of claim 1 wherein said beam is a particle beam.

8. The method of claim 7 wherein said particle beam is an electron beam.

9. The method of claim 1 wherein the maximum potential treatment area of the system extends several tens of centimeters in the x and y directions.

10. The method of claim 1 wherein said beam intensity map is created by the system owner.

11. The method of claim 1 wherein said beam intensity map is provided by a third party.

12. The method of claim 1 wherein the beam intensity map for a particular radiation energy is created by interpolating beam intensity maps at other radiation energy levels.

13. The method of claim 1 further comprising the step of using a flattening filter which does not flatten the beam at at least one beam energy used in the treatment plan.

14. The method of claim 1 wherein the energy of the beam of the radiation therapy system is changed in real time.

15. A method of developing and implementing a radiation treatment plan on a radiation therapy system having a multileaf collimator, comprising:
    obtaining a map of a two-dimensional uneven intensity distribution of a beam of radiation of the therapy system in the proximity of a treatment area at at least one beam energy level,
    developing a treatment plan, comprising,
        determining an irregularly shaped area to be irradiated by the beam of radiation having the two-dimensional uneven intensity distribution,
        dividing the area into one or more portions,
        for each portion, determining one or more energy levels for the radiation beam used to irradiate the portion,
        for each energy level used in each portion, determining the radiation dose to be delivered,
        wherein different portions of the treatment area are irradiated with a radiation beam at different energy levels,
    implementing the treatment plan, said step of implementing the treatment plan for at least one portion comprising a combination of positioning the leaves of the multileaf collimator, and continuously varying the energy level of the radiation beam,
    wherein the positioning of the leaves of the multileaf collimator adjusts for the two-dimensional uneven intensity distribution of the radiation beam.

16. The method of claim 15, wherein said treatment plan comprises irradiating a desired volume from a plurality of different treatment angles.

17. The method of claim 15 wherein the energy of the beam is changed in real time.

18. A method of using a radiation therapy system comprising a multileaf collimator to provide treatment, the radiation system being capable of generating a beam of radiation at at least first and second different energy levels, comprising,
    obtaining information reflecting the intensity distribution of the radiation beam at said first and second beam energies, wherein the intensity distribution of the beam energy at said second energy is not uniform, developing a treatment plan comprising irradiating one or more selected portions of a treatment area with a calculated radiation dose at said second beam energy, implementing the treatment plan, wherein said implementation comprises positioning the leaves of the multileaf collimator and emitting radiation to selectively irradiate said selected portions of the treatment area with said second beam energy wherein said treatment plan comprises using a flattening filter designed to flatten the beam at said first energy level while irradiating the treatment area with a beam at said second energy level.

19. The method of claim 18 wherein the treatment plan comprises irradiating a desired volume from a plurality of different angles.

20. The method of claim 18, wherein said treatment plan comprises changing the energy of the beam in real time.

21. The method of claim 18, wherein said treatment plan comprises varying the energy level of said radiotherapy beam over a range.

22. The method of claim 18 wherein said treatment plan comprises intensity modulated radiotherapy, such that different portions of the treatment area receive different radiation doses.

23. A method of using a radiation therapy system comprising a multileaf collimator to provide treatment, the radiation system being capable of generating a beam of radiation at at least first and second different energy levels, comprising, obtaining information reflecting the intensity distribution of the radiation beam at said first and second beam energies, wherein the intensity distribution of the beam energy at said second energy is not uniform, developing a plurality of treatment plans, at least a first one of said treatment plans comprising irradiating at least a portion of a treatment area with a calculated radiation dose at said first beam energy, and at least a second one of said treatment plans comprising irradiating a portion of the treatment area with a calculated radiation dose at said second beam energy, implementing said second treatment plan, wherein said implementation comprises positioning the leaves of the multileaf collimator and emitting radiation to selectively irradiate said selected portions of the treatment area with said second beam energy using a flattening filter designed for said first beam energy.

24. The method of claim 23 wherein at least one treatment plan provides for changing the energy of the beam of the radiation therapy system in real time.

25. The method of claim 23 wherein at least one treatment plan provides for changing the energy of the radiation beam over a continuous range.

26. The method of claim 23 wherein at least one treatment plan comprises intensity modulated radiotherapy, such that different portions of the treatment area receive different radiation doses.

27. A method of using a radiation therapy system, the radiation system being capable of generating a beam of radiation at at least first and second different energy levels, comprising, irradiating a treatment area with a beam having said second energy level while using a flattening filter designed for a beam having said first energy level.

28. The method of claim 27 further comprising the step of changing the energy of the beam in real time.

* * * * *